United States Patent [19]
McAndrew et al.

[11] Patent Number: 5,880,850
[45] Date of Patent: Mar. 9, 1999

[54] METHOD AND SYSTEM FOR SENSITIVE DETECTION OF MOLECULAR SPECIES IN A VACUUM BY HARMONIC DETECTION SPECTROSCOPY

[75] Inventors: James McAndrew, Lockport; Ronald S. Inman, Lyons, both of Ill.

[73] Assignee: American Air Liquide Inc, Walnut Creek, Calif.

[21] Appl. No.: 951,301

[22] Filed: Oct. 16, 1997

Related U.S. Application Data

[63] Continuation of Ser. No. 711,646, Sep. 10, 1996, abandoned, which is a continuation-in-part of Ser. No. 634,439, Apr. 18, 1996, abandoned.

[60] Provisional application No. 60/005,013 Oct. 10, 1995.

[51] Int. Cl.$^6$ .................................................. G01N 21/00
[52] U.S. Cl. .................... 356/437; 356/436; 250/341.4; 156/345
[58] Field of Search .................................... 356/436, 437, 356/438; 250/335.1, 341.4, 343; 156/345, 625.1; 118/712

[56] References Cited

U.S. PATENT DOCUMENTS

| | | | |
|---|---|---|---|
| 3,524,066 | 8/1970 | Blakkan | 250/218 |
| 3,994,603 | 11/1976 | Paschedag | |
| 4,812,665 | 3/1989 | Puumalainen et al. | 250/341 |

(List continued on next page.)

FOREIGN PATENT DOCUMENTS

| | | |
|---|---|---|
| 0015170 | 9/1980 | European Pat. Off. |
| 0 647 845 | 10/1994 | European Pat. Off. |
| 0647845 | 4/1995 | European Pat. Off. |
| 0 706 042 | 4/1996 | European Pat. Off. |

(List continued on next page.)

OTHER PUBLICATIONS

J. Podolske et al, "Airborne Tunable Diode Laser Spectrometer for Trace–Gas Measurement in the Lower Stratosphere," *Applied Optics*, vol. 32, No. 27, pp. 5324–5333.

(List continued on next page.)

*Primary Examiner*—Frank G. Font
*Assistant Examiner*—Zandra V Smith
*Attorney, Agent, or Firm*—Burns, Doane, Swecker & Mathis, L.L.P.

[57] ABSTRACT

Provided is a novel method and system for harmonic detection spectroscopy. The method comprises providing a cell having a sample region which is circumscribed by at least one wall. The cell has at least one light entry/exit port, with each entry/exit port containing a light transmissive window having a surface facing the sample region and disposed so as to seal the cell in the circumferential direction. A sample gas flows through the sample region in a direction parallel to a cell central axis, and the cell operates at less than atmospheric pressure. A frequency and/or amplitude modulated light source is provided for directing a light beam through one of the at least one light transmissive windows into the cell. The light source modulation amplitude is set to a value which approximately maximizes the value of a harmonic signal at the center of the absorption feature due to the detected gas phase molecular species inside the sample region, and the center frequency of the light source is adjusted so that it is either locked to the center of the absorption feature or repetitively scanned over the frequency range which includes the feature. A spectra is then generated which may be recorded individually or averaged. A detector is provided for measuring the light beam exiting the cell through one of the at least one light transmissive windows. The light source and detector are contained within a chamber which is external to the cell and isolated from the sample region, the chamber and the sample region being placed in optical communication with each other through at least one of the at least one light transmissive windows. The pressure inside the chamber is controlled to a value which is positive relative to atmospheric pressure. The method can be used to detect gas phase molecular species in a sample. Particular applicability is found in semiconductor processing.

37 Claims, 5 Drawing Sheets

U.S. PATENT DOCUMENTS

| | | |
|---|---|---|
| 4,934,816 | 6/1990 | Silver et al. ............................ 356/409 |
| 4,937,461 | 6/1990 | Traina ..................................... 250/575 |
| 4,990,780 | 2/1991 | Lee et al. . |
| 5,024,526 | 6/1991 | von Redwitz . |
| 5,045,703 | 9/1991 | Wieboldt et al. .................... 250/341.4 |
| 5,065,025 | 11/1991 | Doyle . |
| 5,173,749 | 12/1992 | Tell et al. . |
| 5,220,402 | 6/1993 | Harvey . |
| 5,241,851 | 9/1993 | Tapp et al. . |
| 5,294,289 | 3/1994 | Heinz et al. ............................ 156/345 |
| 5,331,409 | 7/1994 | Thurtell et al. . |
| 5,352,902 | 10/1994 | Aoki ....................................... 356/246 |
| 5,453,621 | 9/1995 | Wong . |
| 5,459,574 | 10/1995 | Lee et al. . |
| 5,485,276 | 1/1996 | Bien et al. . |
| 5,517,314 | 5/1996 | Wallin . |
| 5,536,359 | 7/1996 | Kawada et al. ......................... 156/345 |
| 5,550,636 | 8/1996 | Hagans et al. . |
| 5,561,527 | 10/1996 | Krone et al. . |
| 5,578,829 | 11/1996 | Talasek et al. .......................... 250/343 |

FOREIGN PATENT DOCUMENTS

| | | |
|---|---|---|
| 373887 | 4/1996 | European Pat. Off. . |
| 25 04 300 | 11/1975 | Germany . |
| 3633931 | 4/1988 | Germany . |
| 4214840 | 11/1993 | Germany . |
| 2075213 | 11/1981 | United Kingdom . |
| 2165640 | 4/1986 | United Kingdom . |
| WO 90/007 | 1/1990 | WIPO . |
| WO90/00732 | 1/1990 | WIPO . |
| WO94/24528 | 10/1994 | WIPO . |

OTHER PUBLICATIONS

Fried et al, "Application of Tunable Diode Laser Absorption for Trace Stratospheric Measurements of HCL: Laboratory Results," *Applied Optics,* vol. 23, No. 11, Jun. 1984, pp. 1867–1880.

P. Pokrowsky et al, "Sensitive Detection of Hydrogen Chloride by Derivative Spectroscopy with a Diode Laser," *Optical Engineering,* vol. 23, No. 1 (1984), pp. 088–091.

J. Jasinski et al, "Detection of $SiH_2$ in Silane and Dislane Glow Discharges by Frequency Modulation Absorption Spectroscopy,"*Applied Physics Letters,* vol. 44, No. 12, Jun. 1984, pp. 1155–1157.

P.B. Davies et al, "Infrared Laser Diagnostics in Methane Chemical–Vapor–Deposition Plasmas," *Journal of Applied Physics,* vol. 71, No. 12, 15 Jun. 1992, pp. 6125–6135.

Riris et al, "Design of an Open Path Near–Infrared Diode Laser Sensor: Application to Oxygen, Water, and Carbon Dioxide Vaopr Detection," *Applied Optics,* vol. 33, No. 30, Oct. 20, 1994, pp. 7059–7066.

Dreyfus et al, "Optical Diagnostics of Low Pressure Plasmas," Pure & Appl. Chem., vol. 57, No. 9, pp. 1265–1276 (1985).

Lichtman, "Residual Gas Analysis: Past, Present and Future," J. Vac. Sci. Technol. A8(3), pp. 2810–2813 (1990).

Stabb, "Industrielle Gasanalyse Industrial Gas Analysis," *Technisches Messen,* vol. 61, No. 3, Mar. 1, 1994, pp. 133–137.

Mitsui et al., "Development of New APIMS for the Detection of Trace Impurities in Special Gases", Proceedings of the 40th Annual Technical Meeting of the IES, Chicago, pp. 246–253 (1994).

Feher et al, "Tunable Diode Laser Monitoring of Atmospheric Trace Gas Constituents," *Spectrochimica Acta. Part A,* vol. A51, 1995, pp. 1579–1599.

Smoak, Jr. et al, "Gas Control Improves EPI Yield", Semiconductor Int'l., pp. 87–92 (1990).

Atkinson, "High Sensitivity Detection of Water Via Intracavity Laser Spectroscopy,"Microcontamination Conference Proceedings, pp. 98–111 (1994).

Borden, "Monitoring Vacuum Process Equipment: In Situ Monitors—Design and Specification," Microcontamination, vol. 9, No. 1, pp. 43–47 (1991).

White, "Long Optical Paths of Large Aperture", J. Opt. Soc. Am., vol. 32 (1942), pp. 285–288.

Grisar et al, "Fast Sampling Devices for Dynamic Exhaust Gas Analysis," *Proceedings of the 24th ISATA International Symposium on Automotive Technology and Automation,* 20 May 1991, pp. 283–287.

Herriott et al., "Folded Optical Delay Lines", Applied Optics, vol. 4, No. 8, pp. 883–889 (Aug. 1965).

May, "Computer Processing of Tunable Diode Laser Spectra", Applied Spectroscopy, vol. 43, No. 5, 1989, pp. 834–839.

May et al., "Data Processing and Calibration for Tunable Diode Laser Harmonic Absorption Spectrometers", J. Quant. Spectrosc. Radiat. Transfer, vol. 49, No. 4, 1993, pp. 335–347.

Kaur et al, "Multipass cell for molecular beam absorption spectroscopy," *Applied Optics,* Jan. 1, 1990, vol. 29, No. 1, pp. 119–124.

Inman et al., "Application of Tunable Diode Laser Absorption Spectroscopy to Trace Moisture Measurements In Gases," Anal. Chem., vol. 66, No. 15, pp. 2471–2479 (1994).

T. A. Hu et al, "Improved Multipass Optics for Diode Laser Spectroscopy", Review of Scientific Instruments, vol. 64, No. 12, Dec. 1993, pp. 3380–3383.

Patent Abstracts of Japan, vol. 6, No. 59, JP 57–1953, Jan. 1982.

Fried et al., "Versatile Integrated Tunable Diode Laser System For High Precision: Application For Ambient Measurements of OCS", Applied Optics, vol. 30, No. 15, May 20, 1991, pp. 1916–1932.

May et al., "Correlation–Based Technique For Automated Tunable Diode Laser Scan Stabilization", Rev. Sci. Instrum., vol. 63, No. 5, May 1992, pp. 2922–2926.

Eng et al., "Tunable Diode Laser Spectroscopy: An Invited Review", Optical Engineering, Nov./Dec. 1980, vol. 19, No. 6, pp. 945–960.

Lundqvist et al., "Measurements of Pressure–Broadening Coefficients of NO and $O_3$ Using a Computerized Tunable Diode Laser Spectrometer", Applied Optics, vol. 21, No. 17, Sep. 1, 1982, pp. 3109–3113.

Ahlberg et al., "IR–Laser Spectroscopy for Measurement Applications in the Industrial Environment", TR 85170, Dec. 85.

Höjer et al., "Measurements of Electric Field Strength in Gas Insulated High–Voltage Components Using Infrared Diode Laser Absorption Spectroscopy", Applied Optics, vol. 25, No. 17, Sep. 1, 1986, pp. 2984–2987.

Cassidy, "Trace Gas Detection Using 1.3µm InGaAsP Diode Laser Transmitter Modules", Applied Optics, vol. 27, No. 3, Feb. 1, 1988, pp. 610–614.

Webster et al., "Infrared Laser Absorption: Theory and Applications", Wiley, New York, pp. 163–272 (1988).

Wilson, "Modulation Broadening of NMR and ESR Line Shapes", J. App. Phys., vol. 34, No. 11, pp. 3276–3285 (1963).

Mucha et al., "Infrared Diode Laser Determination of Trace Moisture In Gases", ISA Transactions, vol. 25, No. 3, pp. 25–30 (1986).

METHOD AND SYSTEM FOR SENSITIVE DETECTION OF MOLECULAR SPECIES IN A VACUUM BY HARMONIC DETECTION SPECTROSCOPY

This application is a continuation of application Ser. No. 08/711,646, filed Sep. 10, 1996, which is a continuation-in-part of application Ser. No. 08/634,439, filed Apr. 18, 1996, which claims the benefit of priority to Provisional Application No. 60/005,013, filed Oct. 10, 1995.

BACKGROUND OF THE INVENTION

1. Field of the Invention

The present invention relates to a method for detecting gas phase molecular species in a sample by harmonic detection absorption spectroscopy, and to a method for detecting the same in a semiconductor processing apparatus. The present invention also relates to a system for detecting gas phase molecular species in a sample by harmonic detection absorption spectroscopy, and to a semiconductor processing apparatus comprising the same.

2. Description of the Related Art

Semiconductor integrated circuits (ICs) are manufactured by a series of processes, many of which involve the use of gaseous materials. Included among such processes are etching, diffusion, chemical vapor deposition (CVD), ion implantation, sputtering and rapid thermal processing. In these processes, contact is made between a semiconductor substrate and molecular species in the gas phase. As a result of the extremely fine features of the IC devices, parts per billion (ppb) and lower levels of impurities in the gases contacting the semiconductor substrates are usually considered necessary in order to minimize yield loss. Among the molecular impurities, moisture is extremely difficult to eliminate, and it adversely affects many semiconductor manufacturing processes.

A known method for detecting molecular species is infrared absorption spectroscopy. This method is based on the measurement of infrared light absorption which occurs at specific frequencies characteristic of a given molecule. However, when this method is used to measure trace quantities of molecular species inside a vacuum chamber, the measurement precision is often limited by light absorption due to the presence of the same species outside the chamber, where the light source and detector are disposed.

Three methods for mitigating the above described problem have been proposed. The first involves making the light path outside the vacuum chamber as short as possible relative to the path inside, the second is purging the light path outside the vacuum chamber with a pure gas and the third is to place this light path under vacuum. As used herein, the term "pure gas" refers to a gas with a moisture content of essentially zero. The second and third procedures can also be combined by evacuating prior to measurement.

However, these procedures are of limited effectiveness. For example, if the partial pressure of the molecular species of interest inside the vacuum chamber is very low, significant interference can still occur despite these precautions. In particular, when the molecular species of interest is water, components outside of the vacuum chamber often outgas water at a level sufficient to interfere with the measurement. In addition to outgassing, leaks and poorly purged volumes imposed by the geometry of the path outside the chamber can also contribute to the interference. These undesired sources of molecular species are extremely difficult or impossible to completely eliminate, thereby preventing accurate measurements from being made.

In infrared absorption spectroscopy, the absorption of light occurs with a spread about the center absorption frequency which increases linearly with pressure. Therefore, the width of the light absorption due to the molecules in the higher pressure region outside of the vacuum chamber is greater than the width due to the molecules in the lower pressure region inside the vacuum chamber. Additionally, the maximum light absorption at the center frequency is directly proportional to the partial pressure of the species of interest and inversely proportional to the width of the transition. Consequently, as the total pressure of the gas outside the vacuum chamber is increased, the width of the transition also increases.

When a simple infrared absorption measurement is used, no advantage is obtained by increasing the pressure outside of the vacuum chamber, even though the width of the signal due to molecules in that region is increased, because the partial pressure of the species of interest increases proportionately (assuming the concentration of the species remains constant), the signal due to the molecules outside the vacuum chamber is not suppressed because of the cancellation of the two effects. In fact, there would be a slight enhancement the size of which is dependent upon the Doppler linewidth. As a result, the molecular species in the light path outside of the vacuum chamber cannot be negated. Therefore infrared absorption spectroscopy is not suitable for precisely measuring trace quantities of the molecular species inside the vacuum chamber.

According to another known spectroscopic method, harmonic detection spectroscopy, the greater width of the transition due to molecules outside the vacuum chamber can be advantageously used. A more general discussion of the following may be found in C. R. Webster et al. *Infrared Laser Absorption: Theory and Applications in Laser Remote Chemical Analysis*, Wiley, N.Y. (1988).

In the case where the water vapor is in an air or nitrogen matrix at a pressure of 1 atmosphere or higher, the shape of the absorption feature is described by the well-known Lorentz profile as follows:

$$I_0(v) - I(v) = \frac{1}{\pi} \frac{PclS\gamma}{(v - v_0)^2 + \gamma^2}$$

where $I_0(v)$ is the incident light intensity at frequency v, $I(v)$ is the transmitted light intensity at v, P is the pressure, c is the volume concentration of water vapor, l is the length of the light path through the sample, S is the linestrength characteristic of the given absorption feature, $\gamma$ is the half-width of the absorption feature and $v_0$ is its center frequency. This expression gives a maximum light absorption:

$$I_0(v_0) - I(v_0) = \frac{1}{\pi} \frac{PclS}{\gamma}$$

when the frequency of the incident light is $v_0$.

In the case of infrared light absorption by water vapor under vacuum conditions, i.e., at a very low partial pressure (e.g., less than about 0.1 torr, with a total gas pressure in the chamber of no more than about 0.5 torr), absorption features are much narrower. Absorption feature width is determined primarily by the Doppler effect, and results from the random motion of molecules with respect to the incident light, and is described by the following expression (Gaussian lineshape):

$$I_0(v) - I(v) = \frac{1}{\gamma_{ED}\sqrt{\pi}} \frac{PclS}{\exp\left(\frac{v-v_0}{\gamma_{ED}}\right)^2}$$

In the above equation, $\gamma_{ED}\sqrt{\ln(2)}$ is the half-width of the absorption feature under the above conditions, and depends on the center frequency of the absorption frequency, the molecular mass and the temperature. The line-center signal is given by the formula:

$$I_0(v_0) - I(v_0) = \frac{PclS}{\gamma_{ED}\sqrt{\pi}}$$

For water vapor under vacuum conditions and at room temperature i.e., about 25° C., $\gamma_{ED}$ is approximately equal to 0.01 cm$^{-1}$ for absorption of infrared light at frequencies near 7100 cm$^{-1}$ (where relatively strong absorption features accessible by convenient near-infrared diode laser sources are located). For water vapor in a matrix of air or nitrogen at one atmosphere pressure, a typical value of $\gamma$ is 0.1 cm$^{-1}$. The value of $\gamma$ depends on the pressure and temperature of the gaseous sample and the center frequency of the absorption feature. For a given absorption feature at constant temperature, $\gamma$ is approximately described by the following formula:

$$\gamma = \gamma_{ED} + Pb$$

where b is a constant. A more accurate equation has been provided by Olivero and Longbotham, but the above is sufficient for purposes of this discussion.

In order to carry out harmonic detection, the frequency of the incident light source is modulated, with a sinusoidal modulation of amplitude a and frequency $\omega$ so that the frequency of light at time t is given by the expression:

$$v_{mod}(t) = v + a\cos\omega t$$

For first harmonic detection, that component of the signal at the detector which has a frequency $\omega$ and the same phase as the laser modulation is selected. This can be achieved, for example, by using a lock-in amplifier or by using a mixer to combine the detector output with a sinusoidal signal of frequency $\omega$, whose phase is suitably adjusted using a phase shifter, and passing the mixer output through a suitable low-pass filter. A detailed description may be found in *The Art of Electronics* by Horowitz and Hill. This technique is well-known and is used to remove noise components with a frequency of less than $\omega$ from the signal.

In second harmonic detection, the component of the signal with frequency $2\omega$ is selected, in third harmonic detection, the component of the signal with frequency $3\omega$ is selected, and so forth.

For the case of water vapor in nitrogen or air at one atmosphere pressure, the second harmonic signal at $v_0$ (line center) is given by the formula:

$$\text{Signal}(v_0) = \frac{2}{\pi} \frac{PclS}{\gamma} \int_0^\pi \frac{\cos(2\theta)d\theta}{\left(\frac{a\cos\theta}{\gamma}\right)^2 + 1}$$

Similarly, for the case of water vapor under vacuum conditions, $$\text{Signal}(v_0) = \frac{2}{\sqrt{\pi}} \frac{PclS}{\gamma_{ED}} \int_0^\pi \frac{\cos(2\theta)d\theta}{\exp\left(\frac{a\cos\theta}{\gamma_{ED}}\right)^2}$$

These expressions were derived by G. V. H. Wilson, J. Appl. Phys. Vol. 34 No. 11 p. 3276 (1963), who also showed that the maximum value of Signal ($v_0$) is obtained when a/$\gamma$ (or a/$\gamma_{ED}$)=2.2 for both cases.

Second harmonic spectroscopy may be implemented either by setting the frequency of light v emitted by the light source equal to the center frequency of the absorption feature $v_0$ or by repetitively scanning the frequency over a region which includes $v_0$. The former method usually requires active feedback control of the light source if it is a laser diode. In the latter case, scans over the entire absorption feature of interest are obtained. In either case, it is most advantageous if the signal at $v_0$ is primarily due to absorption by water molecules in the sample region of interest.

Figure 1:
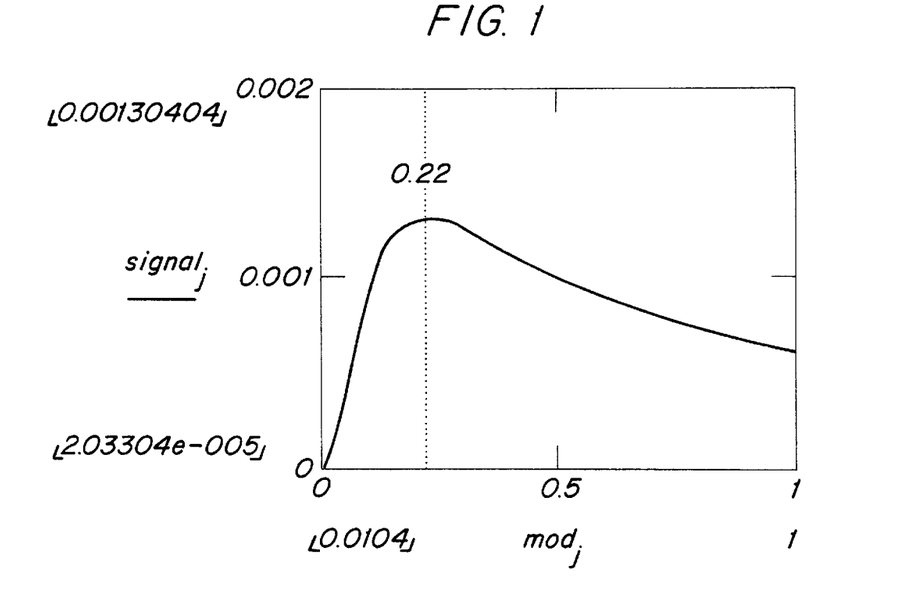
FIG. 1 is a graph that depicts the second harmonic signal at the center of the absorption region for a total pressure of 1 atmosphere versus modulation amplitude.

FIG. 1 is a plot of Signal$_j$, which is obtained from Signal($v_0$) by setting $\gamma$=0.1, Pl S=1 (for ease of calculation, as only relative values are of interest), c=10$^{-6}$ and a=mod$_j$, where mod$_j$ varies between 0 and 1. It can be seen from FIG. 1 that Signal$_j$ is a maximum when mod$_j$=0.22 (i.e. 2.2·0.1), and that the signal becomes lower for smaller values of the modulation amplitude. It follows then, that for a sample under vacuum wherein the ambient outside the vacuum chamber is at atmospheric pressure, if the modulation amplitude is set to 2.2 times the width of the absorption due to the molecular species of interest inside the vacuum chamber, this modulation amplitude will necessarily be much less than the optimum value for the same molecular species outside the chamber.

However, in practice, when it is desired to detect a small partial pressure of a molecular species such as water in a vacuum chamber, and this species is present in the light path outside the chamber, a modulation amplitude which is less than the optimum value for detection of molecules inside the chamber has been used. Sub-optimum modulation amplitudes are purposely chosen as they further suppress the signal due to the higher pressure molecules outside the vacuum chamber.

The above advantages of harmonic spectroscopy for suppressing signals due to molecules at atmospheric pressure in the light path outside the chamber has been recognized by Mucha, ISA Transactions, Vol.25, No.3, p.25 (1986). Mucha further notes the existence of an optimum modulation amplitude which balances suppression of the atmospheric pressure signals with optimization of the signals due to molecules inside the vacuum chamber. In this regard, in previous work of the presently named inventors, Inman et al, *Application of Tunable Diode Laser Absorption Spectroscopy to Trace Moisture Measurements in Gases*, Anal. Chem., Vol.66, No.15, pp.2471–2479 (1994), the Mucha technique was implemented by applying modulation amplitudes from 1.3 to 1.8 times the linewidth due to species inside the chamber.

However, as a result of the use of sub-optimum modulation amplitudes, this technique suffers the disadvantage of a considerable signal loss by up to a factor of four when compared with the signal theoretically obtainable, resulting in a lack of sensitivity and ability to measure trace quantities of molecular species inside a vacuum chamber.

To meet the requirements of the semiconductor processing industry and to overcome the disadvantages of the prior art, it is an object of the present invention to provide a novel method for detecting gas phase molecular species in a sample by harmonic detection spectroscopy which will allow for accurate in situ determination of gas phase molecular species in a sample at a level at least as low as in the ppb range.

It is a further object of the present invention to provide a method for detecting gas phase molecular species in a semiconductor processing apparatus by harmonic detection spectroscopy, using the inventive method.

It is a further object of the present invention to provide a system for detecting gas phase molecular species in a sample by harmonic detection spectroscopy, for practicing the inventive method.

It is a further object of the present invention to provide a semiconductor processing apparatus which includes the inventive system for detecting gas phase molecular species in a sample by harmonic detection spectroscopy.

Other objects and aspects of the present invention will become apparent to one of ordinary skill in the art on a review of the specification, drawings and claims appended hereto.

SUMMARY OF THE INVENTION

The foregoing objectives are achieved by the methods, system and apparatus of the present invention. According to a first aspect of the invention, a novel method for detecting gas phase molecular species in a sample by harmonic detection spectroscopy is provided. The method comprises providing a cell having a sample region which is circumscribed by at least one wall. The cell has at least one light entry/exit port, with each entry/exit port containing a light transmissive window having a surface facing the sample region and disposed so as to seal the cell in the circumferential direction. A sample gas flows through the sample region in a direction parallel to a cell central axis, and the cell operates at less than atmospheric pressure.

A frequency (or wavelength) modulated light source is provided for directing a light beam through one of the at least one light transmissive windows into the cell. The light source modulation amplitude is set to a value which approximately maximizes the value of a harmonic signal at the center of the absorption feature due to the detected gas phase molecular species inside the sample region. The center frequency of the light source is adjusted so that it is either locked to the center of the absorption feature or repetitively scanned over the frequency range which includes the feature. A spectra is then generated which may be recorded individually or averaged.

A detector is provided for measuring the light beam exiting the cell through one of the at least one light transmissive windows. The light source and detector are contained within a chamber which is external to the cell and isolated from the sample region, the chamber and the sample region being placed in optical communication with each other through at least one of the at least one light transmissive windows. The pressure inside the chamber is controlled to a value which is positive relative to atmospheric pressure.

A second aspect of the invention is a method for detecting gas phase molecular species in a semiconductor processing apparatus by harmonic detection spectroscopy, using the inventive method described above with reference to the first aspect of the invention.

A third aspect of the invention is a system for detecting gas phase molecular species in a sample by harmonic detection spectroscopy for practicing the inventive method described above with reference to the first aspect of the invention.

According to a fourth aspect of the invention, a semiconductor processing apparatus is provided. The apparatus comprises a vacuum chamber in communication with a vacuum pump for evacuating the vacuum chamber, for practicing the inventive method with reference to the second aspect of the invention.

BRIEF DESCRIPTION OF THE DRAWINGS

The objects and advantages of the invention will become apparent from the following detailed description of the preferred embodiments thereof in connection with the accompanying drawings, in which like numerals designate like elements, and in which.

DETAILED DESCRIPTION OF THE PREFERRED EMBODIMENTS OF THE INVENTION

The harmonic detection spectroscopy method of the present invention includes providing a cell having a sample region which is circumscribed by at least one wall. The cell has at least one light entry/exit port therein, and each entry/exit port contains a light transmissive window having a surface facing the sample region and disposed so as to seal the cell in the circumferential direction. A sample gas flows through the sample region in a direction parallel to a cell central axis, and the cell operates at less than atmospheric pressure.

A frequency (or wavelength) modulated light source is provided for directing a light beam through one of the at least one light transmissive windows into the cell. The light source modulation amplitude is set to a value which approximately maximizes the value of a harmonic signal at the center of the absorption feature due to the detected gas phase molecular species inside the sample region. For example, in the case of the second harmonic this value is approximately 2.2 times the width of the spectral feature due to the detected gas phase molecular species inside the sample region. For the fourth harmonic, this value is approximately 3.9 times the width of the spectral feature due to the detected gas phase molecular species inside the sample region.

The center frequency of the light source, i.e., that frequency about which modulation occurs, may either be locked to the center of the absorption feature or may be repetitively scanned over the frequency range which includes the feature. Spectra are generated which may be recorded individually or averaged as desired. When the center frequency is repetitively scanned over the spectral region of interest, such scans should occur at a rate which is slow compared to the modulation frequency.

A detector is provided for measuring the light beam exiting the cell through one of the at least one light transmissive windows. The light source and detector are contained within a chamber which is external to the cell and isolated from the sample region. The chamber and the sample region are placed in optical communication with each other through at least one of the at least one light transmissive windows. The pressure inside the chamber is controlled to a value which is positive relative to atmospheric pressure.

The methods and system of the present invention are particularly well suited for overcoming the problems associated with spectroscopic measurements of molecular species in a vacuum chamber. These problems stem in part from interference due to light absorption caused by the presence of the same molecular species in the light path external to the vacuum chamber. In particular, by the present invention, Applicants have prevented or minimized the adverse effects caused by this interference by containing in a pressurized chamber that portion of the light path which is located outside of the vacuum chamber/measurement cell. The pressurized chamber is suitable for operation under positive pressures relative to atmospheric pressure.

Figure 2A:
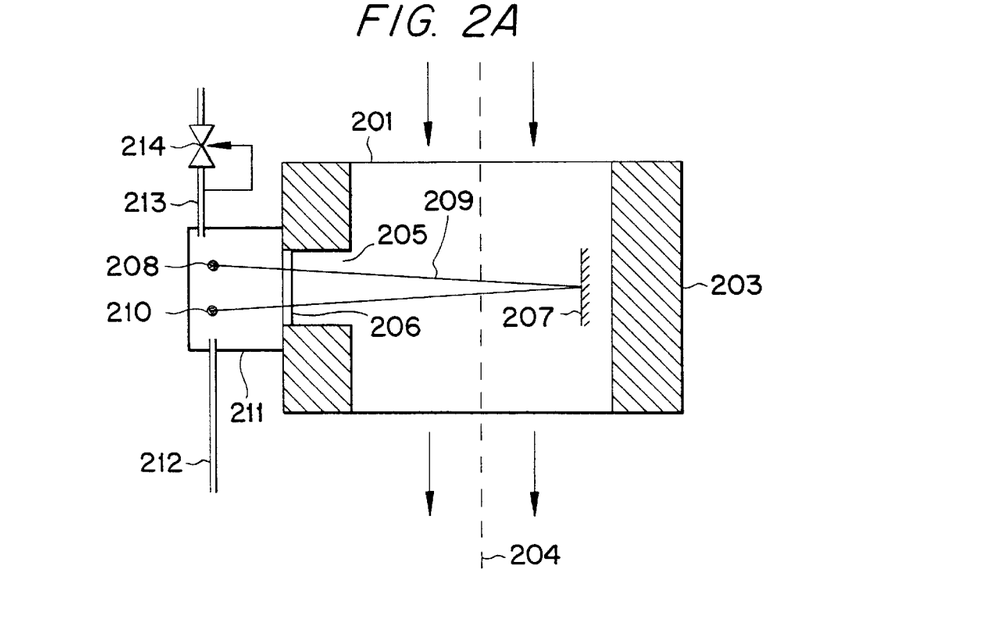
FIGS. 2A and 2B illustrate a cross-sectional and perspective view, respectively, of a system for detecting gas phase molecular species according to the present invention.
Figure 2B:
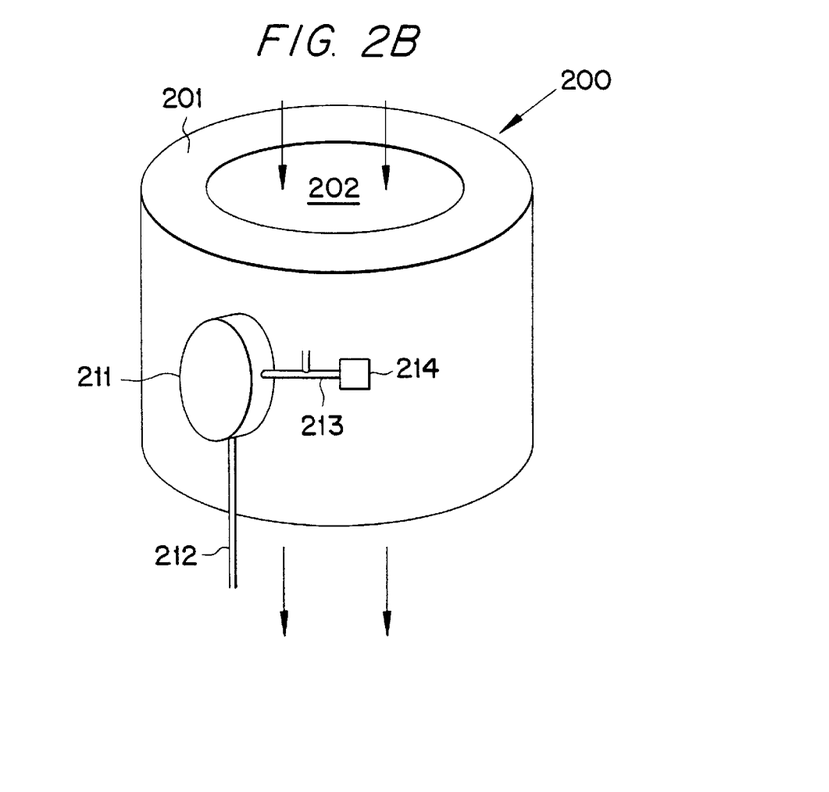

One aspect of the present invention will now be discussed with reference to FIGS. 2A and 2B, which illustrate in cross-sectional and perspective views, respectively, a system for detecting gas phase molecular species.

The inventive system 200 comprises an absorption spectroscopy cell 201 which allows for in situ detection of molecular species in a gas sample. The cell 201 has a sample region 202 which contains a sample to be measured. The sample region is circumscribed by a wall or a plurality of walls 203. The cell 201 further includes an opening extending along the longitudinal axis 204 thereof which extends through the cell. This arrangement allows a sample to pass through the cell in the direction parallel to the cell central axis (indicated by arrows).

One or more light entry/exit ports 205 are included in the walls of the cell, with each entry/exit port containing a light transmissive window 206 which faces the sample region. Together, the cell walls and light transmissive windows seal the cell in the circumferential direction. To form a seal suitable for vacuum environments, an O-ring or other conventional vacuum sealing material can be used.

The cell further comprises at least one light reflective surface 207 such as a mirror for reflecting a light beam within the cell 201. This light reflective surface 207 is preferably a polished metal.

Also included in the system is a light source 208 which can be a frequency modulated light source, preferably a diode laser. Light source 208 directs a light beam 209 through a light transmissive window 206 into the cell sample region 202, where the beam is reflected from light reflective surface 207.

Any molecular impurity of interest can be detected, subject only to the availability of a suitable light source. For example, water vapor, nitric oxide, carbon monoxide and methane or other hydrocarbons can be detected by measuring the attenuation of light from a diode laser source which emits light of a wavelength characteristic of the impurity.

Laser light sources which emit light in spectral regions where the molecules of interest absorb most strongly lead to improvements in measurement sensitivity. In particular, light sources which emit at wavelengths longer than about 2 $\mu$m are preferred, since many of the molecular impurities of interest have strong absorption bands in this region.

Any suitable wavelength-tunable light source can be used. Of the currently available light sources, diode laser light sources are preferred because of their narrow linewidth (less than about $10^{-3}$ cm$^{-1}$) and relatively high intensity (about 0.1 to several milliwatts) at the emission wavelength.

Examples of diode lasers include Pb-salt and GaAs-type diode lasers. The Pb-salt-type laser requires cryogenic temperatures for operation and emits infrared light (i.e., wavelength greater than 3 $\mu$m), while the GaAs-type diode laser can operate at close to room temperature and emits in the near infrared region (0.8–2 $\mu$m).

Recently, diode lasers which include Sb in addition to GaAs (or other pairs of III–V compounds such as AsP) have been described (see, "Mid-infrared wavelengths enhance trace gas sensing," R. Martinelli, Laser Focus World, March 1996, p. 77). These diodes emit light of a wavelength greater than 2 $\mu$m while operating at –87.8° C. While such a low temperature is not convenient, it compares favorably with the cryogenic temperatures (less than –170° C.) required by Pb-salt lasers. Operation of similar lasers at 4 $\mu$m and 12° C. has also been reported (see, Lasers and Optronics, March 1996). Diode lasers of the above described type will most preferably operate at temperatures of at least –40° C. Use of a thermoelectric cooler for temperature control at such temperatures makes these light sources less complicated than the lower temperature diode systems. To make use of these lasers more desirable, improvement in the optical properties over current levels is important. For example, single mode diodes (i.e., diodes whose emission at fixed temperature and drive current is at a single wavelength with emission at other wavelengths at least 40 dB less intense) should be available.

Suitable light sources for use in the invention are not limited to the above described diode lasers. For example, other types of lasers which are similarly sized and tunable by simple electrical means, such as fiber lasers and quantum cascade lasers, are envisioned. The use of such lasers as they become commercially available is envisioned.

The light source modulation amplitude is set a value which approximately maximizes the value of a harmonic signal at the center of the absorption feature due to the detected gas phase molecular species in the sample region. This value is 2.2 times the width of the spectral feature due to the detected gas phase molecular species inside the sample region, for the second harmonic. For the fourth harmonic, this value is 3.9 times the width of the spectral feature.

The center frequency of the light source, i.e., that frequency about which modulation occurs, may either be locked to the center of the absorption feature or may be repetitively scanned over the frequency range which includes the feature. Spectra are generated which may be recorded individually or averaged as desired. When the center frequency is repetitively scanned over the spectral region of interest, such scans should occur at a rate which is slow compared to the modulation frequency.

To detect the light beam 209 after it passes through the sample region and exits the cell through the light transmissive window, detector 210, which is preferably a photodiode, is provided.

Those skilled in the art will readily be able to design the appropriate means for performing frequency modulation, the means for adjusting the center frequency of the light source and the means for generating spectra by use of well known devices, circuits and/or processors and means for their control. Further discussion of the facilitation of frequency modulation and/or control and spectra generation is omitted as it is deemed within the scope of those of ordinary skill in the art.

further include a gas exhaust line 213. In addition, a suitable gas flow restrictor 214, such as an orifice or a back-pressure regulator can be included on the gas exhaust line.

When used in series with a vacuum chamber and vacuum pump system, the cell is capable of operation at less than atmospheric pressure, i.e., under vacuum conditions. In this case, because the pressurized chamber 211 and cell 201 are isolated from one another, the pressurized chamber can be maintained at pressures above atmospheric pressure.

It has further been determined that by optimizing the ratio of the pressure inside the pressurized chamber to the pressure inside the cell, the percentage of total signal due to molecules in the inner chamber can be maximized relative to the total signal due to molecules in the outer chamber. The ratio of the second harmonic signal due to molecules outside the chamber to the total signal is provided by the following formula:

$$secharm_j = \frac{\left| \int_0^\pi \frac{P_j \cdot \cos(2 \cdot \theta)}{\left[ \left( \frac{a \cdot \cos(\theta)}{\gamma_j} \right)^2 + 1 \right]} d\theta \right| \cdot \frac{1}{\pi \cdot \gamma_j}}{\left| \int_0^\pi \frac{P_j \cdot \cos(2 \cdot \theta)}{\left[ \left( \frac{a \cdot \cos(\theta)}{\gamma_j} \right)^2 + 1 \right]} d\theta \right| \cdot \frac{1}{\pi \cdot \gamma_j} + \left| \int_0^\pi \frac{\cos(2 \cdot \theta)}{\exp\left[ \left[ \frac{(a \cdot \cos(\theta))}{\gamma_{ED}} \right]^2 \right]} d\theta \right| \cdot \frac{1}{\gamma_{ED} \cdot \sqrt{\pi}}}$$

Both the light source 208 and detector 210 are contained within a pressurized chamber 211 which is disposed external to the cell 201. To allow the light beam to pass between the pressurized chamber and the cell sample region, the pressurized chamber and the sample region are in optical communication with each other through at least one light transmissive window. However, the respective atmospheres within the pressurized chamber and sample region are isolated from each other.

The system can further include means for controlling the pressure inside the pressurized chamber 211 to a value which is positive relative to atmospheric pressure. The pressure level in the pressurized chamber can be maintained either with or without the use of a gas flow. Should a gas flow be used, suitable gases include pure or inert gases such as, e.g., nitrogen, argon and helium. These gases can be introduced into the pressurized chamber 211 through a pressurizing gas inlet line 212. The pressurized chamber can The numerator is equivalent to the expression given previously for the second harmonic signal due to water vapor in the presence of one atmosphere or higher pressure of air or nitrogen. The denominator is the sum of the same expression with the previously given expression for the second harmonic signal due to water vapor under vacuum conditions.

Likewise, the fourth harmonic signal for the same case is given by the formula:

$$fourharm_j = \frac{\left| \int_0^\pi \frac{P_j \cdot \cos(4 \cdot \theta)}{\left[ \left( \frac{v - a \cdot \cos(\theta)}{\gamma_j} \right)^2 - 1 \right]} d\theta \right| \cdot \frac{1}{\pi \cdot \gamma_j}}{\left| \int_0^\pi \frac{P_j \cdot \cos(4 \cdot \theta)}{\left[ \left( \frac{v - a \cdot \cos(\theta)}{\gamma_j} \right)^2 - 1 \right]} d\theta \right| \cdot \frac{1}{\pi \cdot \gamma_j} + \left| \int_0^\pi \frac{\cos(4 \cdot \theta)}{\exp\left[ \left[ \frac{(v - a \cdot \cos(\theta))}{\gamma_{ED}} \right]^2 \right]} d\theta \right| \cdot \frac{1}{\gamma_{ED} \cdot \sqrt{\pi}}}$$

For the above, it has been assumed that the pathlength and water partial pressure inside and outside the cell are equal when the pressure outside the cell is one atmosphere, and that the concentration of water vapor outside the cell remains constant as the pressure in that region increases ($P_j$ is in atmospheres). However, extension of these principles to the case where the pathlengths and water partial pressure are unequal is within the level of knowledge of persons having ordinary skill in the art. The modulation amplitude a is assumed to be 2.2 times the Doppler width in the situation in which the second harmonic is being used.

Figure 3:
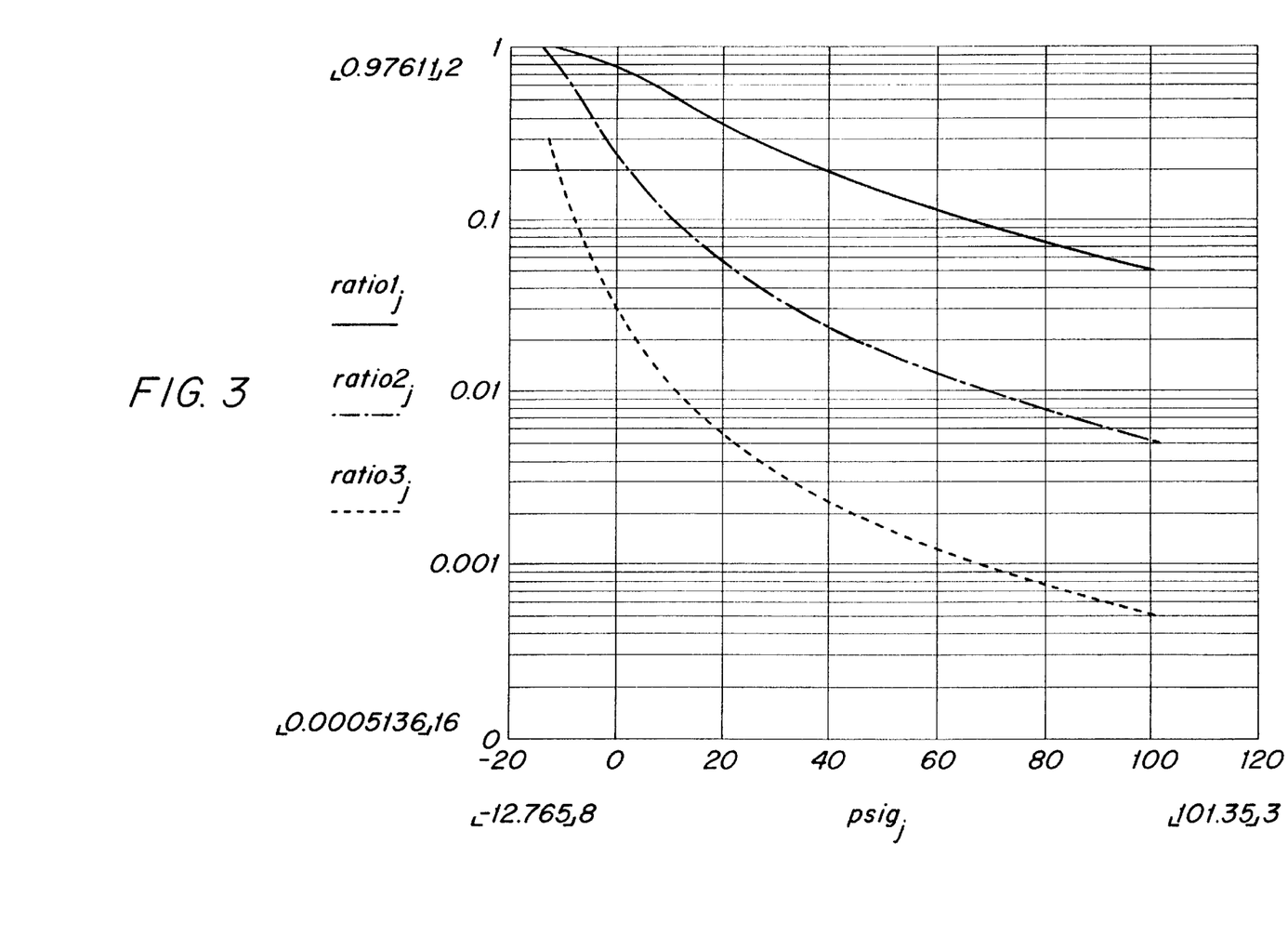
FIG. 3 is a comparative graph that depicts the ratio of the second harmonic signal due to water molecules in the outer chamber to that in the inner chamber versus pressure in the outer chamber for three inner chamber water molecule partial pressures.

As shown in FIG. 3, the above formula was evaluated using values of the parameters appropriate for absorption of light at wavelengths in the region of 1400 nm, due to water vapor, for a concentration of water vapor of 1 ppm (by volume) in nitrogen in the pressurized chamber, and for partial pressures of $10^{-6}$, $10^{-5}$ and $10^{-4}$ torr (ratio 1, ratio 2, and ratio 3, respectively) inside the cell/vacuum chamber. In FIG. 3, the ratio of the second harmonic signal due to water molecules in the outer chamber to the signal in the inner chamber is plotted versus pressure in the pressurized chamber for the three inner chamber partial pressures.

This graph illustrates the general relationship of a decrease in the ratio (i.e., an increase in the signal due to water inside the cell relative to that due to water in the pressurized chamber) with an increase in pressure in the pressurized chamber. For example, for a chamber pressure of one atmosphere (0 psig) and a water vapor pressure in the cell/vacuum chamber of $10^{-6}$ torr, 80% of the total signal will be due to water molecules in the pressurized chamber. This ratio is not acceptable, as it will result in a substantial amount of interference in the measurement unless the partial pressure of the water molecules is exceptionally stable.

Thus, in order to use the optimum modulation amplitude the pressure in the outer chamber should be made as high as possible, but at least 65 psig in order to reduce the contribution from water there to 10% of the total. In addition, for a water vapor partial pressure of $10^{-4}$ torr in the cell/vacuum chamber, water in the pressurized chamber will account for only 3% of the total signal at atmospheric pressure, and operation under these conditions may be feasible. However, as shown in FIG. 3, by increasing the outer pressure to 20 psig one would expect a substantial reduction in the contribution from water molecules in the outer chamber to 0.6% of the total. Further increases in the pressure inside the pressurized chamber in this case would be unlikely to lead to additional benefit since other sources of instability that will lead to fluctuations in the signal on the order of 1% can be expected. The pressure in the cell is preferably less than 1 torr, although some benefit of the invention is obtained at cell pressures up to 1 atmosphere, and between 1 and 5 atmospheres in the chamber.

It has been found that particularly beneficial and unexpected results can be obtained when harmonics other than the second are applied to the present invention. In fact, higher harmonics were found to provide an even better suppression of the signal due to the molecular species in the pressurized chamber as the pressure therein is increased.

Figure 4:
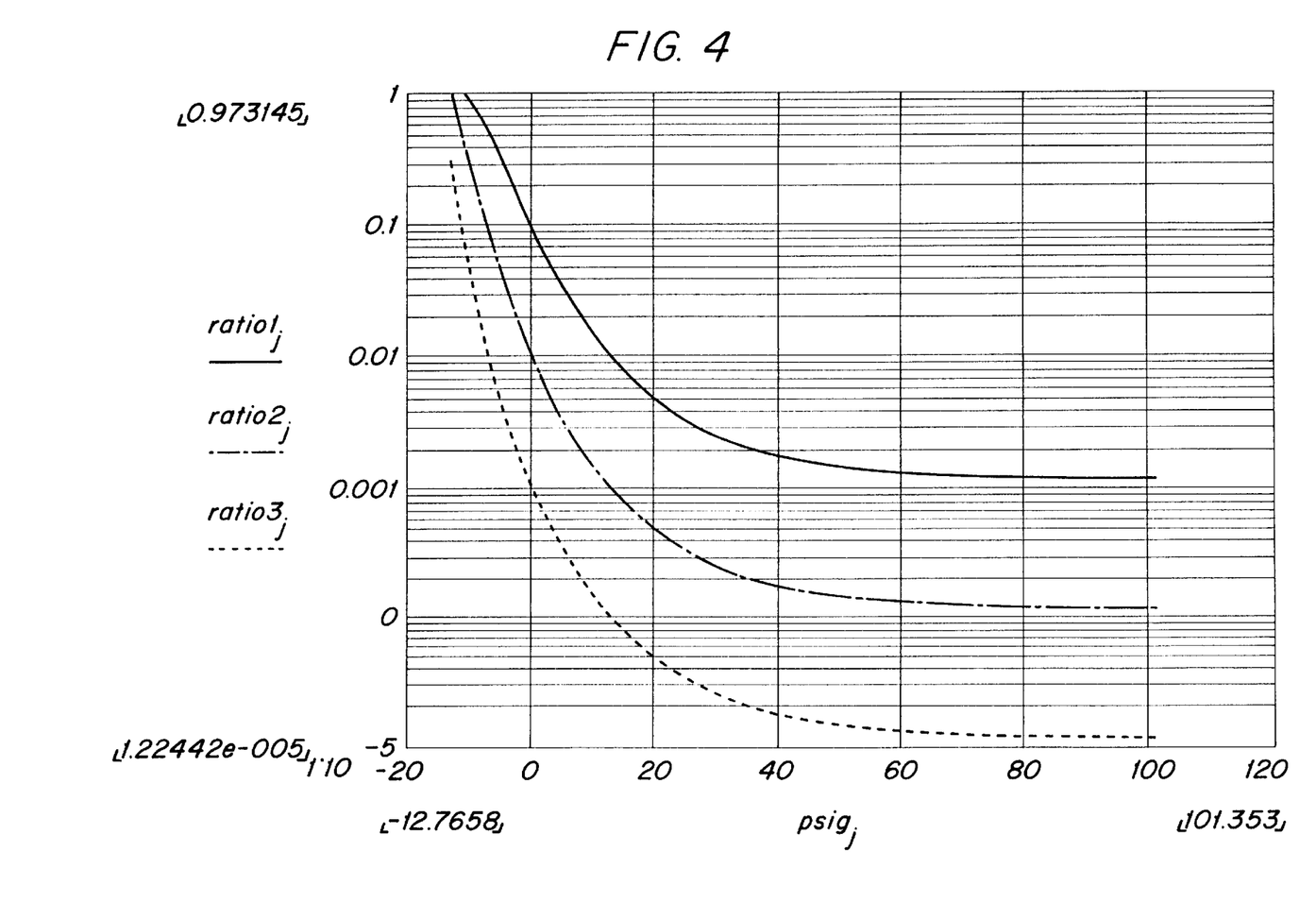
FIG. 4 is a comparative graph that depicts the ratio of the fourth harmonic signal due to water molecules in the outer chamber to that in the inner chamber versus pressure in the outer chamber for three inner chamber water molecule partial pressures.

FIG. 4 is a comparative graph depicting the results obtained for detection of the fourth harmonic from the analogous calculation to that discussed above in reference to FIG. 3, which relates to the second harmonic. In FIG. 4, the ratio of the fourth harmonic signal due to water molecules in the pressurized chamber to that in the inner chamber is plotted against pressure in the pressurized chamber for three inner chamber water molecule partial pressures of $10^{-6}$, $10^{-5}$ and $10^{-4}$ torr (ratio 1, ratio 2, and ratio 3, respectively). As can be seen from this figure, the fourth harmonic generally shows a decrease in the ratio with an increase in pressure of the pressurized chamber. However, for increases beyond a certain pressure, this ratio becomes relatively constant, and further increases in pressure would not lead to further substantial reductions in the ratio.

Figure 5:
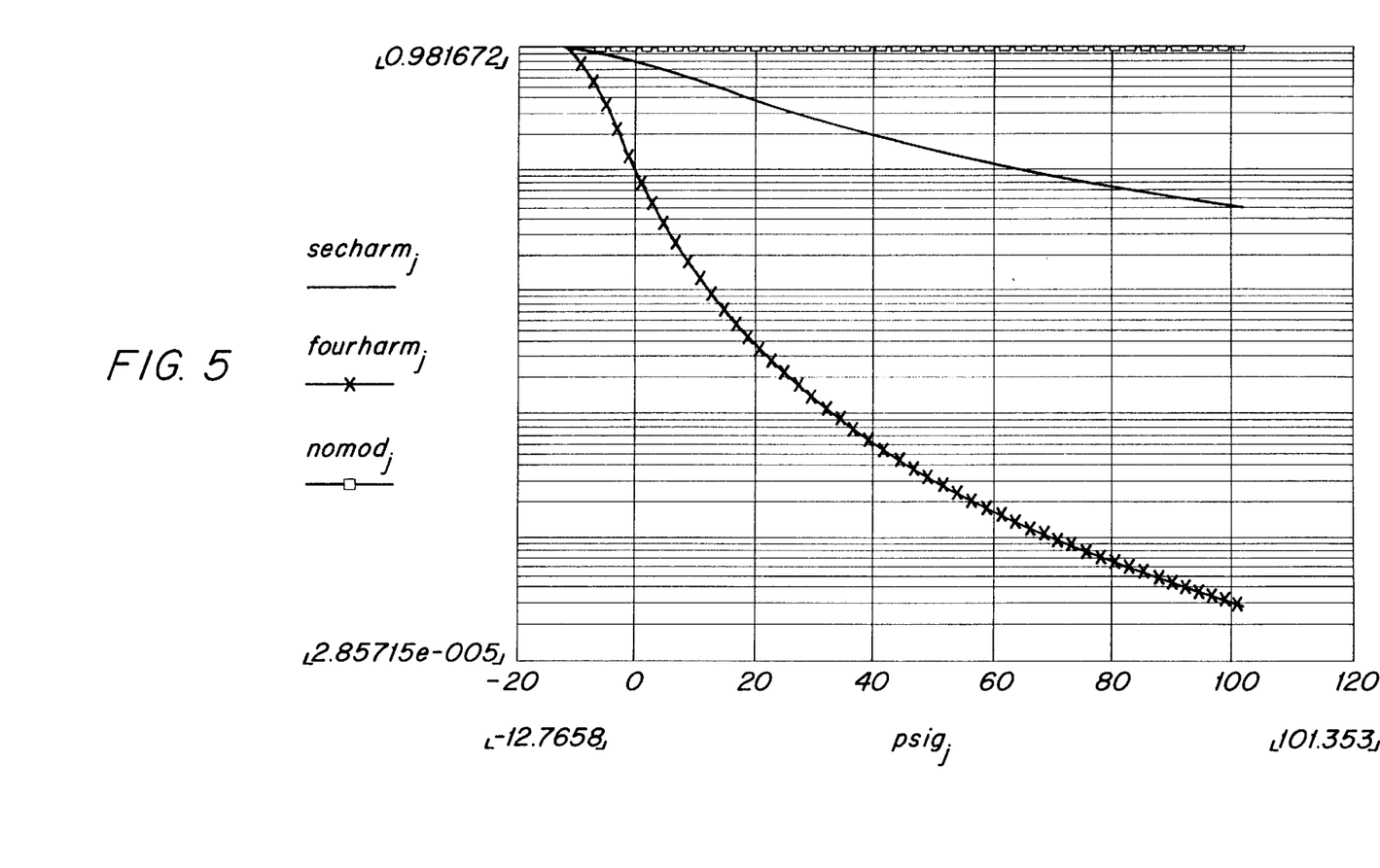
FIG. 5 is a comparative graph that depicts the ratio of the signal due to water molecules in the outer chamber to that in the inner chamber versus pressure in the outer chamber for second and fourth harmonic detection, and for detection with no modulation of the light source frequency.

FIG. 5 illustrates the relative benefit of pressurizing the outer chamber for the case of second harmonic detection (secharm), fourth harmonic detection (fourharm) and detection without any modulation of the light source frequency (nomod), for the case where the partial pressure of water and the pathlength in the inner and the outer chamber are equal. It can be seen that where there is no modulation, no advantage is obtained from pressurization. Second harmonic detection with atmospheric pressure in the outer chamber results in 80% absorption by water in the outer chamber, which, as mentioned previously, is unacceptable. Increasing the outer chamber pressure to 65 psig will result in a contribution of 10% of the total signal from water vapor in this chamber, which should be acceptable. However, it is preferable in this case to use fourth harmonic detection, which, even when the pressure in the outer chamber is one atmosphere, leads to a contribution of 10% by water vapor in that chamber, and, when coupled with a modest pressurization of 15 psig of the outer chamber, can reduce the contribution from water in that chamber to less than 1%.

The novel system described above allows for in situ detection of molecular species in a gas exhausted from a vacuum chamber, and has the capability of operation at up to high or even ultra-high vacuum levels. In such a case, the cell can be disposed between a vacuum chamber and vacuum pump system. The system is compatible with a wide range of materials. For example, the vacuum chamber can contain reactive or nonreactive (inert) gases which can be in a plasma- or non-plasma state. Examples of reactive gases which are compatible with the inventive system include $SiH_4$ HCl and $Cl_2$ provided the moisture level is less than 1000 ppm. Inert gases such as, e.g., $O_2$, $N_2$, Ar and $H_2$ can also be used in the inventive system. In the case of the inventive system's use in a plasma environment, the system is preferably mounted about 6 inches or more away from the plasma zone in order to minimize formation of deposits on the windows and other cell surfaces.

Because the system described above in reference to FIGS. 2A and 2B can be used in a variety of atmospheres, the system is particularly well suited for use in monitoring molecular species in a semiconductor processing apparatus. Use of the system in conjunction with a semiconductor processing apparatus allows for real-time *in situ* detection of gas phase molecular impurities which is of particular importance in minimizing yield loss.

Figure 6:
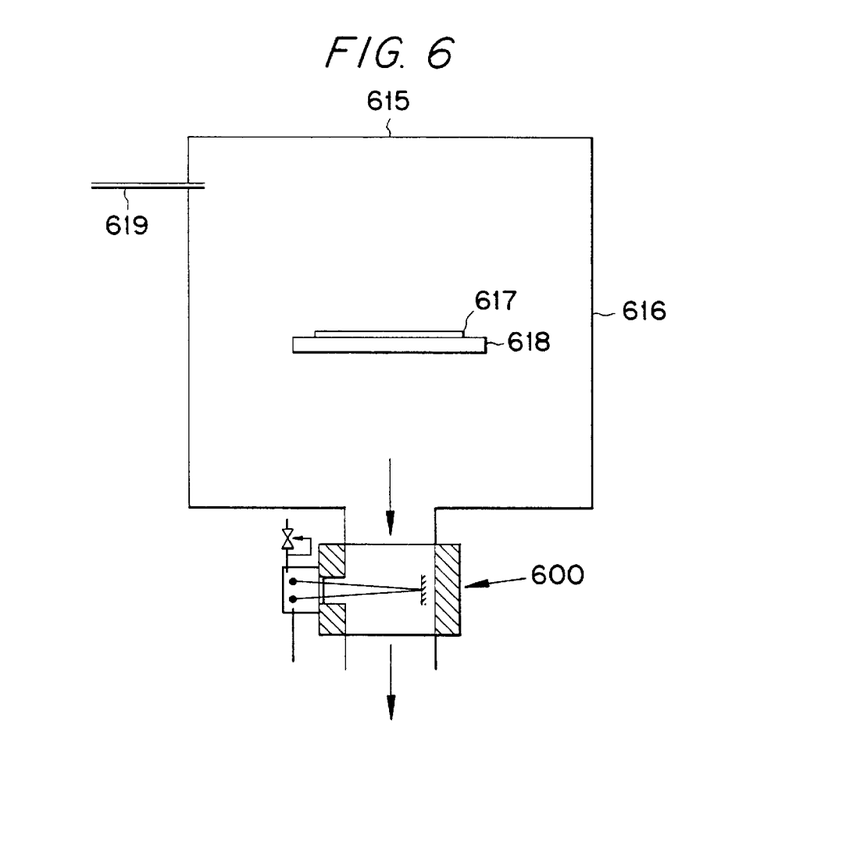
FIG. 6 illustrates in cross-section, a semiconductor processing apparatus which includes the system for detecting gas phase molecular species according to the present invention.

One example of such a configuration is shown in FIG. 6. The illustrated apparatus 615 comprises a vacuum chamber 616 inside which a semiconductor substrate 617 is disposed on a substrate holder 618. A process gas inlet 619 is provided for delivering a gas or plural gases to the vacuum chamber. The vacuum chamber is evacuated through an exhaust opening 620 in the vacuum chamber. A vacuum pump (not shown) for evacuating the vacuum chamber is connected to the chamber, either directly or through a vacuum line. A pump exhaust line can be connected to the pump, which can be connected to another pump or to a gas scrubber. Examples of vacuum pumps which may be employed are mechanical, booster and rotary pumps, diffusion pumps, cryogenic pumps, sorption pumps and turbomolecular pumps. The system has been described in detail above in reference to FIGS. 2A and 2B.

While the inventive system 600 has been illustrated as being disposed below the vacuum chamber, those skilled in the art will readily appreciate that other orientations are also possible. While the structure of the semiconductor processing apparatus has been shown generically in FIG. 6, persons skilled in the art will readily appreciate that the system can be adapted to virtually any of the semiconductor processing apparatuses employing a vacuum system. Examples of such apparatuses are etching, diffusion, chemical vapor deposition (CVD), ion implantation, sputtering and rapid thermal processing apparatuses.

While the invention has been described in detail with reference to specific embodiments thereof, it will be apparent to one skilled in the art that various changes and modifications can be made, and equivalents employed, without departing from the scope of the appended claims.

What is claimed is:

1. A method for detecting gas phase molecular species in a sample by harmonic detection spectroscopy, comprising:

providing a cell having a sample region which is circumscribed by at least one wall, the cell having at least one light entry/exit port therein, each entry/exit port containing a light transmissive window having a surface facing the sample region and disposed so as to seal the cell in the circumferential direction, wherein a sample gas flows through the sample region in a direction parallel to a cell central axis, the cell operating at about atmospheric pressure or less;

providing a frequency and/or amplitude modulated light source for directing a light beam through one of the at least one light transmissive windows into the cell and setting the light source modulation amplitude to a value which approximately maximizes the value of a harmonic signal at the center of the absorption feature due to the detected gas phase molecular species inside the sample region;

adjusting the center frequency of the light source so that it is either locked to the center of the absorption feature or repetitively scanned over the frequency range which includes the feature, generating spectra which may be recorded individually or averaged as desired;

providing a detector for measuring the light beam exiting the cell through one of the at least one light transmissive windows;

wherein the light source and detector are contained within a chamber which is external to the cell and isolated from the sample region, the chamber and the sample region being placed in optical communication with each other through at least one of the at least one light transmissive windows, and controlling the pressure inside the chamber to a value which is positive relative to atmospheric pressure.

2. The method for detecting gas phase molecular species according to claim 1, wherein the harmonic signal is a second harmonic signal, and the modulation amplitude is set to approximately 2.2 times the width of the spectral absorption feature due to the detected gas phase molecular species in the sample region.

3. The method for detecting gas phase molecular species according to claim 1, wherein the harmonic signal is a fourth harmonic signal, and the modulation amplitude is set to approximately 3.9 times the width of the spectral absorption feature due to the detected gas phase molecular species in the sample region.

4. The method for detecting gas phase molecular species according to claim 1, further comprising controlling the pressure inside the chamber to approximately maximize the percentage of the measured signal due to the detected gas phase molecular species in the chamber.

5. The method for detecting gas phase molecular species according to claim 4, wherein the chamber pressure is controlled by use of an orifice or a back pressure regulator.

6. The method for detecting gas phase molecular species according to claim 1, further comprising introducing a pressurizing gas into the chamber and optionally exhausting gas from the chamber.

7. The method for detecting gas phase molecular species according to claim 1, wherein the frequency and/or modulated light source is a diode laser.

8. The method for detecting gas phase molecular species according to claim 1, wherein the molecular species is water vapor.

9. The method for detecting gas phase molecular species according to claim 1, wherein the molecular species is detected in a gas exhausted from a vacuum chamber, or from a chamber operated at approximately atmospheric pressure.

10. The method for detecting gas phase molecular species according to claim 9, wherein the cell is disposed between and in communication with a vacuum chamber and a vacuum pump.

11. The method for detecting gas phase molecular species according to claim 10, wherein the vacuum chamber forms a portion of a semiconductor processing apparatus.

12. The method for detecting gas phase molecular species according to claim 11, wherein the semiconductor processing apparatus is selected from the group consisting of an etching apparatus, a chemical vapor deposition apparatus, an ion implantation apparatus, a sputtering apparatus and a rapid thermal processing apparatus.

13. The method for detecting gas phase molecular species according to claim 12, wherein the semiconductor processing apparatus is an etching apparatus.

14. The method for detecting gas phase molecular species according to claim 1, further comprising generating a plasma in the vacuum chamber.

15. The method for detecting gas phase molecular species according to claim 1, further comprising introducing a reactive gas into the vacuum chamber.

16. A method for detecting gas phase molecular species in a semiconductor processing apparatus by harmonic detection spectroscopy, comprising:

providing a vacuum chamber in communication with a vacuum pump and evacuating the vacuum chamber therewith;

providing a cell having a sample region which is circumscribed by at least one wall, the cell having at least one light entry/exit port therein, each entry/exit port containing a light transmissive window having a surface facing the sample region and disposed so as to seal the cell in the circumferential direction, wherein a sample gas flows through the sample region in a direction parallel to a cell central axis, the cell operating at about atmospheric pressure or less;

providing a frequency and/or amplitude modulated light source for directing a light beam through one of the at least one light transmissive windows into the cell and setting the light source modulation amplitude to a value which approximately maximizes the value of a harmonic signal at the center of the absorption feature due to the detected gas phase molecular species inside the sample region;

adjusting the center frequency of the light source so that it is either locked to the center of the absorption feature or repetitively scanned over the frequency range which includes the feature, generating spectra which may be recorded individually or averaged as desired;

providing a detector for measuring the light beam exiting the cell through one of the at least one light transmissive windows;

wherein the light source and detector are contained within a chamber which is external to the cell and isolated from the sample region, the chamber and the sample region being placed in optical communication with each other through at least one of the at least one light transmissive windows, and controlling the pressure inside the chamber to a value which is positive relative to atmospheric pressure.

17. The method for detecting gas phase molecular species according to claim 16, wherein the harmonic signal is a second harmonic signal, and the modulation amplitude is set to approximately 2.2 times the width of the spectral absorption feature due to the detected gas phase molecular species in the sample region.

18. The method for detecting gas phase molecular species according to claim 16, wherein the harmonic signal is a fourth harmonic signal, and the modulation amplitude is set to approximately 3.9 times the width of the spectral absorption feature due to the detected gas phase molecular species in the sample region.

19. The method for detecting gas phase molecular species according to claim 16, wherein the pressure inside the chamber is set to approximately maximize the percentage of a total signal due to the detected gas phase molecular species in the chamber.

20. A system for detecting gas phase molecular species in a sample by harmonic detection spectroscopy, comprising:
   a cell having a sample region which is circumscribed by at least one wall, the cell having at least one light entry/exit port therein, each entry/exit port containing a light transmissive window having a surface facing the sample region and disposed so as to seal the cell in the circumferential direction, wherein a sample gas flows through the sample region in a direction parallel to a cell central axis, the cell being capable of operation at less than atmospheric pressure;
   a frequency and/or amplitude modulated light source system comprising a light source for directing a light beam through one of the at least one light transmissive windows into the cell, means for setting the light source modulation amplitude to a value which approximately maximizes the value of a harmonic signal at the center of the absorption feature due to the detected gas phase molecular species inside the sample region;
   means for adjusting the center frequency of the light source so that it is either locked to the center of the absorption feature or repetitively scanned over the frequency range which includes the feature, means for generating spectra which may be recorded individually or averaged;
   a detector for measuring the light beam exiting the cell through one of the at least one light transmissive windows;
   wherein the light source and detector are contained within a chamber which is external to the cell and isolated from the sample region, the chamber and the sample region being in optical communication with each other through at least one of the at least one light transmissive windows, and means for controlling the pressure inside the chamber to a value which is positive relative to atmospheric pressure.

21. The system for detecting gas phase molecular species according to claim 20, wherein the harmonic signal is a second harmonic signal, and the modulation amplitude is approximately 2.2 times the width of the spectral absorption feature due to the detected gas phase molecular species in the sample region.

22. The system for detecting gas phase molecular species according to claim 20, wherein the harmonic signal is a fourth harmonic signal, and the modulation amplitude optimum value is approximately 3.9 times the width of the spectral absorption feature due to the detected gas phase molecular species in the sample region.

23. The system for detecting gas phase molecular species according to claim 20, wherein the pressure inside the chamber is set to maximize the percentage of a total signal due to the detected gas phase molecular species in the chamber.

24. The system for detecting gas phase molecular species according to claim 20, wherein the chamber pressure control means comprises a pressurizing gas inlet and an exhaust gas outlet connected to the chamber.

25. The system for detecting gas phase molecular species according to claim 24, wherein the chamber pressure control means further comprises an orifice or a back pressure regulator.

26. The system for detecting gas phase molecular species according to claim 20, wherein the frequency and/or modulated light source is a diode laser.

27. The system for detecting gas phase molecular species according to claim 20, wherein the molecular species is water vapor.

28. The system for detecting gas phase molecular species according to claim 20, wherein the cell is disposed between and in communication with a vacuum chamber and a vacuum pump.

29. The system for detecting gas phase molecular species according to claim 28, wherein the vacuum chamber forms a portion of a semiconductor processing apparatus.

30. The system for detecting gas phase molecular species according to claim 29, wherein the semiconductor processing apparatus is selected from the group consisting of an etching apparatus, a chemical vapor deposition apparatus, an ion implantation apparatus, a sputtering apparatus and a rapid thermal processing apparatus.

31. The system for detecting gas phase molecular species according to claim 30, wherein the semiconductor processing apparatus is an etching apparatus.

32. The system for detecting gas phase molecular species according to claim 28, wherein the vacuum chamber is adapted to contain a plasma atmosphere.

33. The system for detecting gas phase molecular species according to claim 28, wherein the vacuum chamber is adapted to contain a reactive gas atmosphere.

34. A semiconductor processing apparatus, comprising:
   a vacuum chamber in communication with a vacuum pump for evacuating the vacuum chamber;
   a system for detecting gas phase molecular species in a sample by harmonic detection spectroscopy comprising a cell having a sample region which is circumscribed by at least one wall, the cell having at least one light entry/exit port therein, each entry/exit port containing a light transmissive window having a surface facing the sample region and disposed so as to seal the cell in the circumferential direction, wherein a sample gas flows through the sample region in a direction parallel to a cell central axis, the cell being capable of operation at less than atmospheric pressure;
   a frequency and/or amplitude modulated light source system comprising a light source for directing a light beam through one of the at least one light transmissive windows into the cell, means for setting the light source modulation amplitude to a value which approximately maximizes the value of a harmonic signal at the center of the absorption feature due to the detected gas phase molecular species inside the sample region, means for adjusting the center frequency of the light source so that it is either locked to the center of the absorption feature or repetitively scanned over the frequency range which includes the feature and means for generating spectra which may be recorded individually or averaged;

a detector for measuring the light beam exiting the cell through one of the at least one light transmissive windows;

wherein the light source and detector are contained within a chamber which is external to the cell and isolated from the sample region, the chamber and the sample region being in optical communication with each other through at least one of the at least one light transmissive windows, and means for controlling the pressure inside the chamber to a value which is positive relative to atmospheric pressure.

35. The system for detecting gas phase molecular species according to claim 34, wherein the harmonic signal is a second harmonic signal, and the modulation amplitude is approximately 2.2 times the width of the spectral absorption feature due to the detected gas phase molecular species in the sample region.

36. The system for detecting gas phase molecular species according to claim 34, wherein the harmonic signal is a fourth harmonic signal, and the modulation amplitude is approximately 3.9 times the width of the spectral absorption feature due to the detected gas phase molecular species in the sample region.

37. The system for detecting gas phase molecular species according to claim 34, wherein the pressure inside the chamber is set to maximize the percentage of a total signal due to the detected gas phase molecular species in the chamber.

* * * * *